(12) United States Patent
Yano et al.

(10) Patent No.: US 6,214,575 B1
(45) Date of Patent: Apr. 10, 2001

(54) β-CAROTENE HYDROXYLASE GENE

(75) Inventors: Masamitsu Yano; Mitsuo Omura; Yoshinori Ikoma; Akira Komatsu, all of Shizuoka (JP)

(73) Assignees: Director General of National Institute of Fruit Tree Science, Ministry of Agriculture, Forestry and Fisheries, Ibaraki; Bio-Oriented Technology Research Advancement Institution, Saitama, both of (JP)

( * ) Notice: Subject to any disclaimer, the term of this patent is extended or adjusted under 35 U.S.C. 154(b) by 0 days.

(21) Appl. No.: 09/198,092

(22) Filed: Nov. 23, 1998

(30) Foreign Application Priority Data

Dec. 2, 1997 (JP) .................................................. 9-331936

(51) Int. Cl.$^7$ .............................. C12P 23/00; C12N 9/02; C12N 15/53; C12N 15/70
(52) U.S. Cl. ......................... 435/67; 435/69.1; 435/189; 435/252.3; 435/252.33; 435/320.1; 536/23.2
(58) Field of Search ............................. 435/320.1, 252.3, 435/252.33, 189, 67; 536/23.2

(56) References Cited

FOREIGN PATENT DOCUMENTS 0 747 483 A2    11/1996  (EP) .
WO 91/13078     9/1991   (WO) .
WO 97/36998     10/1997  (WO) .

OTHER PUBLICATIONS

A. Ruther et al., "Production of zeaxanthin in *Escherichia coli* transformed with different carotenogenic plasmids" Appl. Microbiol. Biotechnol. (1997) 48:162–167.

Sun et al., "Cloning and Functional Analysis of the –Carotene Hydroxylase of *Arabidopsis thaliana*" The Journal of Biological Chemistry, vol. 271, No. 40, Issue of Oct. 4, pp. 24349–24352 (1996).

Hundle et al., "In vitro expression and activity of lycopene cyclase and –carotene hydroxylase from *Erwina herbicola*" FEBS 11977, vol. 315, No. 3, 329–334.

*Primary Examiner*—Ponnathapu Achutamurthy
*Assistant Examiner*—William W. Moore
(74) *Attorney, Agent, or Firm*—Fish & Richardson P.C.

(57) ABSTRACT

The present invention provides a β-carotene hydroxylase and a DNA coding for the enzyme. The DNA of the invention codes for the following recombinant protein (a) or (b):

(a) a protein consisting of the amino acid sequence as shown in SEQ ID NO: 2;

(b) a protein which consists of the amino acid sequence as shown in SEQ ID NO: 2 having deletion, substitution or addition of one or several amino acids and which has β-carotene hydroxylase activity.

6 Claims, 3 Drawing Sheets

FIG. 3

```
Peptide
Score Table: Unitary Matrix
GAP Penalty: -4

CitBECH1                        1:MAVGLLAAIVPKPFCLLLTTKLQPSSLLTTKPAPLFAPLGTHHGFFNGKNRRKLNSFTVCFVLEEKKQSTQIETFTDEEEEESGTQISTA-
Arabidopsis                     1:--------------------------------FSSSSTDFRLR.PKSLSG.-SPSL.-FKR.S..Y.V..RR.NSP..NDERP.STS.TNA.DAEY
Agrobacterium aurantiacum-crtZ  1:-----------------------------------------------------------------------------------------
Alcaligenes sp-crtZ             1:-----------------------------------------------------------------------------------------
Erwinia herbicola crtZ          1:-----------------------------------------------------------------------------------------
Erwinia uredovora-crtZ          1:-----------------------------------------------------------------------------------------

CitBECH1                       91:-A-RVAEKLARKRSERFTYLVAAVMSSFGITSMAVMAVYYRFWNQMEGGEVPLAEMFGTFALSVGAAVGMEFWARWAHKALWHASLWHMH
Arabidopsis                    91:L.L.L....E..K..S...I.ML.....................S.......ISML......TNFLIVVATVL.MELTAYSVHRWIMHGPLG.GW.
Agrobacterium aurantiacum-crtZ 91:.............................................................TNFLIVVATVL.MELTAYSVHRWIMHGPLG.GW.
Alcaligenes sp-crtZ            91:.............................................................TQFLIVVATVL.MELTAYSVHRWIMHGPLG.GW.
Erwinia herbicola crtZ         91:-----------------------------------------------------MLVNSLIVILSVIAMEGIA.FTHRYIMHG-WG.RW.
Erwinia uredovora-crtZ         91:-----------------------------------------------------MLWIWNNALIVF.TVIGMEVIA.LAHKYIMHG-WG.GW.
                                                                                                             *          *

CitBECH1                      181:ESHHRPREGPFELNDVFAIINAVPAIALLSFGFFHKGLVPGLCFGAGLGITVFGMAYMFVHDGLVHKRFPVGPIADVPYFRRVAAAHQLH
Arabidopsis                   181:...K............V..G...G..Y..N..........I...................L.K.....
Agrobacterium aurantiacum-crtZ 181:K....EEHDHAL.K..LYGLVF..I.TV.FTV.WIWAPVLWW----IA..M.Y.LI.FVL......Q.W.FRY.PRKG.A..LYQ..R..
Alcaligenes sp-crtZ           181:K....EEHDHAL.K..LYGVVF..L.TI.FTV.AYWWPVLWW----IA..M.Y.LI.FIL......Q.W.FRY.PRRG...LYQ..R..
Erwinia herbicola crtZ        181:...T..K.V...L..VVF.GV...IAV.TAGVWPLQW----I.C.M..Y.LL.FL......Q.W.FHW.PRRG.LK.LYV..R..
Erwinia uredovora-crtZ        181:L....E..K.A..V..LY.VVF.ALS.L.IYL.STGMWPLQW----I.A.M.AY.LL.FM.......Q.W.FRY.PRKG.LK.LYM..RM.
                                             ***                                  *          ******           **    *

CitBECH1                      271:HSDKFHGVPYGLFLGPKELEEVGGLEELEKEISKRIKSYNRVPK------
Arabidopsis                   271:T...N...............N...D....R.....KKASGSGSSSSS
Agrobacterium aurantiacum-crtZ 271:.AVEGRDHCVSFGFIYAPPVDKLKQDLKMSGVLRAEAQERT--------
Alcaligenes sp-crtZ           271:.AVEGRDHCVSFGFIYAPPVDKLKQDLKRSGVLRPQDERPS--------
Erwinia herbicola crtZ        271:.AVRGREGCVSFGFIYARKPADLQAILR.RHGRPPKRDAAKDRPDAASPSSSSPE--
Erwinia uredovora-crtZ        271:.AVRGKEGCVSFGFLYAPPLSKLQATLR.RHGARAGAARDAQGGEDEPASGK----
```

β-CAROTENE HYDROXYLASE GENE

BACKGROUND OF THE INVENTION

1. Field of the Invention

The present invention relates to a β-catotene hydroxylase, a DNA coding for the β-catotene hydroxylase, a recombinant vector comprising the DNA, a transformant transformed with the vector, a method for preparing the β-catotene hydroxylase and a method for preparing β-cryptoxanthin.

2. Description of the Prior Art

In carotenoids synthesized by animals, plants and microorganisms, there are a group of compounds with a hydroxyl group(s) generically called xanthophyll. These compounds are generated from carotenoids (starting substances) by the catalytic action of hydroxylase. For example, one hydroxyl group is introduced into β-carotene to yield β-cryptoxanthin, into which another hydroxyl group is introduced to yield zeaxanthin via the biosynthetic pathway shown below (see arrow (1) in FIG. 1):

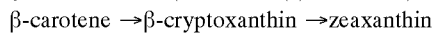

β-carotene →β-cryptoxanthin →zeaxanthin

This β-cryptoxanthin is obtained by introducing a hydroxyl group into one of the two ionone rings present in β-carotene. When another hydroxyl group is introduced into a position symmetric to the former position, zeaxanthin is produced (FIG. 1).

In a large number of plants and microorganisms, metabolism proceeds from β-carotene to zeaxanthin, producing little β-cryptoxanthin, the intermediate into which only one hydroxyl group is introduced.

This reaction is controlled by a hydroxylase gene called Crt Z. In this enzyme reaction, it is considered that two hydroxyl groups are introduced almost simultaneously. For example, under the control of a hydroxylase gene cloned from a bacterium belonging to the genus Erwinia, zeaxanthin is produced which is obtainable by introducing two hydroxyl groups into β-carotene.

In *Citrus unshiu* (*Satsuma mandarine*) which is a major citrus fruit in Japan, β-cryptoxanthin obtainable by introducing one hydroxyl group into β-carotene is considered to be one of the most important carotenoids. In particular, β-cryptoxanthin occupies 60–70% of the total carotenoid content in the edible part of this fruit.

Considering this high β-cryptoxanthin content of *Citrus unshiu*, it is hard to think that the β-cryptoxanthin in *Citrus unshiu* is produced by a gene involved in the above-mentioned metabolic pathway. Also, it is still unknown whether β-cryptoxanthin is produced by those genes which have been already cloned.

OBJECTS AND SUMMARY OF THE INVENTION

It is an object of the present invention to provide a β-carotene hydroxylase and a gene coding for the enzyme.

As a result of intensive and extensive researches toward the solution of the above problem, the present inventors have succeeded in isolating from a citrus-derived cDNA library a DNA coding for a β-carotene hydroxylase. Thus, the present invention has been achieved.

The present invention relates to the following recombinant protein (a) or (b):

(a) a protein consisting of the amino acid sequence as shown in SEQ ID NO: 2;

(b) a protein which consists of the amino acid sequence as shown in SEQ ID NO: 2 having deletion, substitution or addition of one or several amino acids and which has β-carotene hydroxylase activity.

The present invention further relates to a DNA coding for the following protein (a) or (b):

(a) a protein consisting of the amino acid sequence as shown in SEQ ID NO: 2;

(b) a protein which consists of the amino acid sequence as shown in SEQ ID NO: 2 having deletion, substitution or addition of one or several amino acids and which has β-carotene hydroxylase activity.

Further, the present invention relates to a DNA coding for a β-carotene hydroxylase, comprising the nucleotide sequence as shown in SEQ ID NO: 1.

Further, the present invention relates to a recombinant vector comprising the above DNA.

Further, the present invention relates to a transformant which is transformed with the above vector.

Further, the present invention relates to a method for preparing a β-carotene hydroxylase comprising culturing the above transformant in a medium and recovering the β-carotene hydroxylase from the resultant culture.

Further, the present invention relates to a method for preparing β-cryptoxanthin comprising culturing the above transformant in a medium and recovering β-cryptoxanthine from the resultant culture.

BRIEF DESCRIPTION OF THE DRAWINGS

FIG. 3 is a diagram showing comparison of homology in amino acid sequences between the β-carotene hydroxylase of the invention and other enzymes.

DETAILED DESCRIPTION OF THE INVENTION

Figure 1:
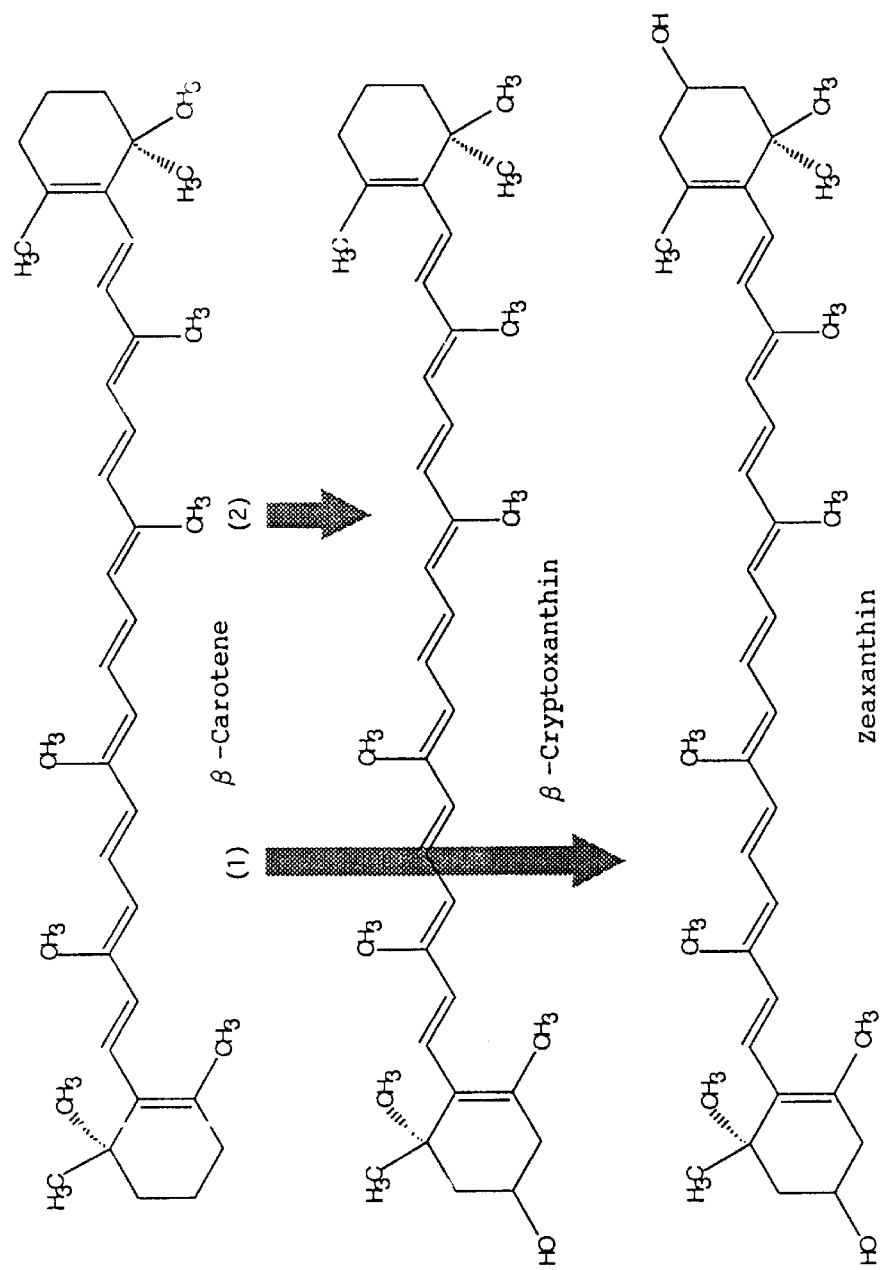
FIG. 1 is a diagram showing a biosynthetic pathway of carotenoids.

The present invention relates to a β-carotene hydroxylase which catalyzes the reaction indicated by arrow (2) in FIG. 1 and a DNA coding for the β-carotene hydroxylase.

The cDNA of the invention can be isolated by the following procedures. Briefly, a primer is designed based on a conserved region of a gene coding for a bacterium-derived β-carotene hydroxylase. Then, 3' RACE RT-PCR is performed using the above primer and, as a template, a first strand cDNA from the fruit (juice sacs) and flower of *Citrus unshiu* (variety: Miyagawa early) to obtain a cDNA fragment of the *Citrus unshiu* β-carotene hydroxylase. Subsequently, using this cDNA fragment as a probe, the β-carotene hydroxylase of interest can be isolated from a cDNA library derived from the edible part of *Citrus unshiu*.

1. Cloning of a DNA Coding for the β-Carotene Hydroxylase (1) Preparation of Primers First, primers for use in the 3' RACE RT-PCR to be described later are prepared. In order to design a primer that is more specific to a DNA of interest, it is appropriate to prepare an oligonucleotide coding for a region in which amino acid residues are highly conserved among various bacteria and plants. Such a primer can be prepared by conventional chemical synthesis. For example, the following amino acid sequences may be selected as regions satisfying the above-mentioned condition:

i) [Phe Glu Leu Asn Asp Val Phe Ala] (SEQ ID NO: 3)
ii) [His Asp Gly Leu Val His] (SEQ ID NO: 4)

Since these two regions with highly conserved amino acid residues are located close to each other, they cannot be used as a sense primer and an antisense primer in a PCR. Thus, in the present invention, 3' RACE RT-PCR method was employed in which each of these sequences was used as a sense primer.

The above sequences are found within the amino acid sequences for an Arabidopsis-derived and an Erwinia-derived β-carotene hydroxylase described by Zairen Sun et al., The Journal of Biological Chemistry, 1996; Vol. 271, No. 40; 24349–24352 and Nakagawa M. and N. Misawa, Agric. Biol. Chem. 55:2147–2148, respectively.

Based on these amino acid sequences, oligonucleotide primers with the following sequences, for example, are prepared. However, the primers are not limited to these sequences.

Sense 1 primer (Bech-a): TT(t/c)GA(g/a)CTAAA(c/t)GA(t/c)GTN (SEQ ID NO: 5)

Sense 2 primer (Bech-B): CACGA(c/t)GGTCTNGTNCA (SEQ ID NO: 6)

(2) 3' RACE RT-PCR

Subsequently, a 3' RACE RT-PCR is performed using the two sense primers synthesized. RT-PCR (reverse transcription-PCR) is a method in which a DNA is synthesized (reverse transcribed) with RNA as a template using a reverse transcriptase, and thereafter a PCR is performed using the synthesized DNA as a template. 3' RACE (rapid amplification of cDNA ends) is a method in which an RT-PCR is performed based on a nucleotide sequence of a known region to thereby clone the unknown region of a cDNA of interest up to the relevant cDNA end.

First, a reverse transcription is performed using an oligo (dT) primer having an adaptor sequence at its 5' end to thereby synthesize a first strand cDNA. All of the resultant first strand cDNA molecules have a structure in which the adaptor sequence is attached to the end. Therefore, in the cDNA to be cloned, the unknown region is located between the known sequence and the adaptor sequence. Then, the unknown region (cDNA partial sequence) sandwiched between the two sequences can be amplified by performing a PCR using a part of the known sequence as a sense primer together with the adaptor primer.

An RT-PCR can be performed using a commercial kit (T-Primed First-Strand Kit: Pharmacia).

(3) Preparation of a cDNA Library

In order to obtain the full-length cDNA of interest from a fruit-derived cDNA library using the cDNA partial sequence obtained above as a probe, the library is prepared as described below.

Total RNA is isolated from individual citrus organs or tissues (fruit, leaf, root, flower, callus, etc.) using a guanidine reagent or SDS-phenol. Then, mRNA is prepared from the total RNA by the affinity column method using oligo dT-cellulose or poly U-Sepharose carried on Sepharose 2B or by a method using an oligotex resin. Using the resultant mRNA as a template, a single-stranded cDNA is synthesized with a reverse transcriptase. Thereafter, a double-stranded CDNA is synthesized from the single-stranded CDNA. The resultant double-stranded cDNA is ligated to an appropriate plasmid or phage vector using a ligase to thereby obtain a recombinant DNA. By infecting or transforming *Escherichia coli* or the like with this recombinant DNA, a cDNA library capable of screening by plaque or colony hybridization can be obtained.

(4) Isolation of a β-Carotene Hydroxylase cDNA Homologue from the cDNA Library

Subsequently, screening for the full-length cDNA sequence is performed by plaque or colony hybridization using the cDNA sequence isolated by the 3' RACE RT-PCR described above as a probe. For this hybridization, a commercial kit such as ECL Nucleic Acid Labelling and Detection System (Amersham) may be used.

(5) Determination of the Nucleotide Sequence

The nucleotide sequence of the obtained clone is determined. This can be performed by conventional methods such as Maxam-Gilbert method, the dideoxy method or the like. Usually, the determination is carried out with an automatic DNA sequencer.

SEQ ID NO: 1 shows the nucleotide sequence for the DNA of the invention and SEQ ID NO: 2 shows the amino acid sequence for the β-carotene hydroxylase of the invention. However, as long as a protein consisting of this amino acid sequence has β-carotene hydroxylase activity, the sequence may have some mutation such as deletion, substitution or addition of one or several amino acids. For example, a protein consisting of the amino acid sequence of SEQ ID NO: 2 in which Met at the first position has been deleted is also included in the protein of the invention.

The β-carotene hydroxylase activity in the present invention means an activity to perform a catalytic reaction producing β-cryptoxanthin from β-carotene.

Once the nucleotide sequence for the DNA of the invention has been established, the DNA of the invention can be obtained by chemical synthesis or by hybridization using a DNA fragment having a part of the sequence as a probe.

2. Preparation of a Recombinant Vector and a Transformant (1) Preparation of a Recombinant Vector The recombinant vector of the invention can be obtained by ligating (inserting) the DNA of the invention to (into) an appropriate vector. The vector into which the DNA of the invention is to be inserted is not particularly limited as long as it is replicable in a host. For example, a plasmid DNA, a phage DNA or the like may be used.

A plasmid DNA can be prepared from *E. coli* or Agrobacterium by alkali extraction (Birnboim, H. C. & Doly, J. (1979), Nucleic Acid Res., 7:1513) or variations thereof. Alternatively, a commercial plasmid such as pBluescript II SK+ (Stratagene), pUC118 (TaKaRa), pUC119 (TaKaRa), pGEM-T (Promega) or the like may be used. It is preferred that these plasmids contain a selectable marker such as ampicillin resistance gene, kanamycin resistance gene or chloramphenicol resistance gene.

As a phage DNA, M13mp18, M13mp19 or the like may be given.

For insertion of the DNA of the invention into a vector, a method may be employed in which the purified DNA is digested with an appropriate restriction enzyme and then inserted into the relevant restriction site or the multi-cloning site of the vector for ligation.

The DNA of the invention should be incorporated in the vector in such a manner that the function thereof is operable. For this purpose, the vector of the invention may contain a terminator, ribosome binding sequence or the like in addition to a promoter and the DNA of the invention.

(2) Preparation of a Transformant

The transformant of the invention can be obtained by introducing the recombinant vector of the invention into a host so that the gene of interest can be expressed.

The host is not particularly limited as long as it can express the DNA of the invention. Specific examples of the host include Escherichia or Bacillus bacteria such as *E. coli* and *Bacillus subtilis*; yeasts such as *Saccharomyces cerevisiae*; or animal cells such as COS cells and CHO cells.

When a bacterium such as *E. coli* is used as the host, preferably, the recombinant vector of the invention is capable of autonomous replication in the host and, at the same time, is constituted by a promoter, a ribosome binding sequence, the DNA of the invention and a transcription termination sequence. The vector may also contain a gene to control the promoter.

As the expression vector, pBluescript II vector (Stratagene), pET vector (Stratagene) or the like may be used.

As the promoter, any promoter may be use as long as it can direct the expression of the DNA of the invention in the host such as *E. coli*. For example, an *E. coli*-derived or phage-derived promoter such as trp promoter, lac promoter, $P_L$ promoter or $P_R$ promoter may be used.

As a method for introducing the recombinant vector into the bacterium, any method of DNA introduction into bacteria may be used. For example, a method using calcium ions (Proc. Natl. Acad. Sci., USA, 69:2110–2114 (1972)) may be used. When a yeast is used as the host, YEp13, YEp24, YCp50or the like is used as an expression vector. As a promoter used in this case, any promoter may be used as long as it can direct the expression of the DNA of the invention in yeasts. For example, gal1 promoter, gal10 promoter, heat shock protein promoter, $MF_\alpha 1$ promoter or the like may be enumerated.

As a method for introducing the recombinant vector into the yeast, any method of DNA introduction into yeasts may be used. For example, electroporation (Methods Enzymol., 194:182–187 (1990)), the spheroplast method (Proc. Natl. Acad. Sci., USA, 84:1929–1933 (1978)), the lithium acetate method (J. Bacteriol., 153:163–168 (1983)) or the like may be enumerated.

When an animal cell is used as the host, pcDNAI/Amp (Invitrogen) or the like is used as an expression vector. In this case, the early gene promoter of human cytomegalovirus or the like may be used as a promoter.

As a method for introducing the recombinant vector into the animal cell, electroporation, the calcium phosphate method, lipofection or the like may be enumerated.

The recombinant vector of the invention incorporated in *E. coli* (designation: EpCitBECH1) was deposited at the National Institute of Bioscience and Human-Technology, Agency of Industrial Science and Technology (1–3, Higashi 1-Chome, Tsukuba City, Ibaraki Pref., Japan) as FERM BP-6188 under the Budapest Treaty.

3. Production of the β-Carotene Hydroxylase

The β-carotene hydroxylase of the invention can be obtained by culturing the transformant described above and recovering the β-carotene hydroxylase from the resultant culture.

The cultivation of the transformant of the invention in a medium is carried out by conventional methods used for culturing a host.

As a medium to culture the transformant obtained from a microorganism host such as *E. coli* or yeast, either a natural or a synthetic medium may be used as long as it contains carbon sources, nitrogen sources and inorganic salt sources assimilable by the microorganism and can be used for effective cultivation of the transformant.

As carbon sources, carbohydrates such as glucose, fructose, sucrose, starch; organic acids such as acetic acid, propionic acid; and alcohols such as ethanol and propanol may be used.

As nitrogen sources, ammonia; ammonium salts of inorganic or organic acids such as ammonium chloride, ammonium sulfate, ammonium acetate, ammonium phosphate; other nitrogen-containing compounds; Peptone; meat extract; corn steep liquor and the like may be used.

As inorganic substances, potassium dihydrogen phosphate, dipotassium hydrogen phosphate, magnesium phosphate, magnesium sulfate, sodium chloride, iron(II) sulfate, manganese sulfate, copper sulfate, calcium carbonate and the like may be used.

Usually, the cultivation is carried out under aerobic conditions (such as shaking culture or aeration agitation culture) at 28° C. for 48 to 60 hrs. During the cultivation, the pH is maintained at 7.0 to 7.5. The pH adjustment is carried out using an inorganic or organic salt, an alkali solution or the like. When an *E. coli* transformant is cultured, it is preferable to allow pACCAR16ΔcrtX plasmid (having 4 Erwinia-derived genes that can produce carotenoids from farnesyl diphosphate to β-carotene) to co-exist in the *E. coli*.

During the cultivation, an antibiotic such as ampicillin or tetracycline may be added to the medium if necessary.

When a microorganism transformed with an expression vector using an inducible promoter is cultured, an inducer may be added to the medium if necessary. For example, when a microorganism transformed with an expression vector using Lac promoter is cultured, isopropyl-β-D-thiogalactopyranoside (IPTG) or the like may be added. When a microorganism transformed with an expression vector using trp promoter is cultured, indoleacetic acid (IAA) or the like may be added.

As a medium to culture a transformant obtained from an animal cell as a host, commonly used RPMI1640 medium or DMEM medium, or one of these media supplemented with fetal bovine serum, etc. may be used.

Usually, the cultivation is carried out in the presence 5% $CO_2$ at 37° C. for 1 to 2 days.

During the cultivation, an antibiotic such as kanamycin or penicillin may be added to the medium if necessary.

After the cultivation, the β-carotene hydroxylase of the invention is recovered by disrupting the microorganisms or cells if the enzyme is produced in the microorganisms or cells. If the β-carotene hydroxylase of the invention is produced outside of the microorganisms or cells, the culture fluid (as it is or after centrifugation to remove the microorganisms or cells) is subjected to conventional biochemical techniques used for isolating/purifyinng a protein. These techniques include ammonium sulfate precipitation, gel chromatography, ion exchange chromatography and affinity chromatography. These techniques may be used independently or in an appropriate combination to isolate and purify the β-carotene hydroxylase of the invention from the culture.

The confirmation that the finally obtained protein is a β-carotene hydroxylase can be made by SDS-polyacrylamide gel electrophoresis.

4. Production of β-Cryptoxanthin

In the present invention, it is also possible to produce β-cryptoxanthin in the same manner as described in the purification of the β-carotene hydroxylase. Briefly, the transformant described above is cultured in a medium and then β-cryptoxanthin is extracted from the resultant culture. The method of cultivation is the same as described in "3. Production of the β-Carotene Hydroxylase".

After the cultivation, the microorganisms or cells are removed from the culture by centrifugation of the like. Then, β-cryptoxanthin can be extracted from the culture by HPLC or the like.

The confirmation that the finally extracted substance is β-cryptoxanthin can be made by $^1$H-NMR, ultraviolet-visible spectroscopy, mass spectrometry, etc.

PREFERRED EMBODIMENTS OF THE INVENTION

Now, the present invention will be described more specifically below with reference to the following Examples, which should not be instrued as limiting the technical scope of the invention.

EXAMPLE 1

Cloning of a cDNA Coding for the β-Carotene Hydroxylase (1) Cloning of a Partial cDNA of Interest Using 3' RACE RT-PCR A 1st-strand cDNA was prepared by performing a reverse transcription using NotI-D(T)$_{18}$(5'd [AACTGGAAGAATTCGCGGCCGCAGGAAT$_{18}$]-3') (SEQ ID NO: 7) as a primer and RNA from the fruit (juice sacs) and flower of *Citrus unshiu* (variety: Miyagawa early) as a template. At the time of this synthesis, NotI adaptor sequence (TGGAAGAATTCGCGGCCGCAG) (SEQ ID NO: 8) was added at the 3' end of every 1st-strand CDNA fragment. Using this 1st-strand CDNA as a template, a PCR was performed with Sense 1 primer and the adaptor primer. The reaction was carried out 35 cycles, 1 cycle consisting of denaturation at 94.5° C. for 40 sec and annealing/extension at 60° C. for 2 min. In this first stage PCR, however, the adaptor primer used is the sequence contained commonly in all of the cDNA fragments generated by the reverse transcription reaction. Therefore, the PCR product obtained at this stage contains a large number of non-specifically amplified DNA fragments. In order to amplify the DNA of interest specifically, the second stage PCR was performed using Sense 2 primer. This reaction was carried out 35 cycles, one cycle consisting of denaturation at 94.5° C. for 35 sec, annealing at 55° C. for 45 sec and extension at 72° C. for 1 min. For the RT-PCR, a commercial kit (T-Primed First-Strand Kit: Pharmacia) was used.

By the above procedures, a cDNA partial sequence coding for a citrus β-carotene hydroxylase was obtained.

(2) Preparation of a cDNA Library from a Citrus Fruit Tissue

Total RNA was isolated from the fruit (juice sac tissue) of *Citrus unshiu* (variety: Miyagawa early) using guanidine thiocyanate. After the isolated total RNA was purified into mRNA using Oligotex-dT30 [Super] (TaKaRa), a first-strand cDNA was synthesized using an oligo(dT)$_{12-18}$ primer and a reverse transcriptase from Moloney murine leukemia virus (MMLV). Further, a second-strand cDNA was synthesized using a DNA polymerase (Pharmacia). To the resultant double-stranded CDNA, EcoRI adaptor was added by T4 DNA ligase, followed by ligation to Uni-ZAP EcoRI phagemid vector (Stratagene).

(3) Screening of the Full-Length CDNA of Interest by Plaque Hybridization

Subsequently, the full-length CDNA sequence of interest was screened by plaque hybridization using the cDNA partial sequence coding for a citrus β-carotene hydroxylase obtained by the 3' RACE RT-PCR described above.

A commercial kit (ECL nucleic acid labelling and detection system: Amersham) was used for the hybridization. As a result of the screening (3×10$^4$ pfc), a β-carotene hydroxylase cDNA homologue of 1158 bp in full length was isolated which was coding for a peptide of 311 amino acid residues with an estimated molecular weight of 34.7 kDa. This clone exhibited 76.3% homology to an Arabidopsis-derived β-carotene hydroxylase cDNA which produces zeaxanthin from β-carotene, and 35.7 to 39.8% homology to bacteria-derived β-carotene hydroxylase genes which produce zeaxanthin. This clone was designated "CitBECH1". The nucleotide sequence for CitBECH1 is shown in SEQ ID NO: 1, and the amino acid sequence encoded by CitBECH1 is shown in SEQ ID NO: 2.

The results of comparison of homology between conventional β-carotene hydroxylases and the β-carotene hydroxylase of the invention are shown in FIG. 3.

In FIG. 3, shown at the top row (CitBECH1) is the β-carotene hydroxylase amino acid sequence encoded by the gene of the invention. The others are amino acid sequences encoded by related genes; any of these sequences is a sequence for a gene producing zeaxanthin from β-carotene skipping over β-cryptoxanthin.

EXAMPLE 2

Production of β-Cryptoxanthin in *Escherichia coli* Having the β-Carotene Hydroxylase (1) Expression of the DNA of the Present Invention The isolated clone was inserted into pBluescript II SK+ plasmid having an ampicillin resistance gene. The resultant plasmid was introduced into *Escherichia coli*, in which pACCAR16ΔcrtX plasmid (having 4 Erwinia-derived genes that can produce from farnesyl diphosphate to β-carotene) was allowed to co-exist. The resultant *E. coli* was cultured in LB medium at 28° C. for 60 hrs.

Then, the culture was subjected to acetone extraction. The acetone extract from the transformant was subjected to HPLC using a system manufactured by Japan Spectroscopic Co., Ltd. As a column, a C30 column manufactured by YMC was used. As eluent A, a mixture of methanol/methyl-t-butyl ether/water mixed at a ratio of 81/15/4 was used. As eluent B, a mixture of methanol/methyl-t-butyl ether mixed at a ratio of 10/90 was used. Gradient conditions were as follows: eluent A 100% at the time of start; eluent A 20% and eluent B 80% 70 min after the start. The flow rate was 1.0 ml/min and the column temperature 22° C. The detection wave length was 450 nm.

Figure 2:
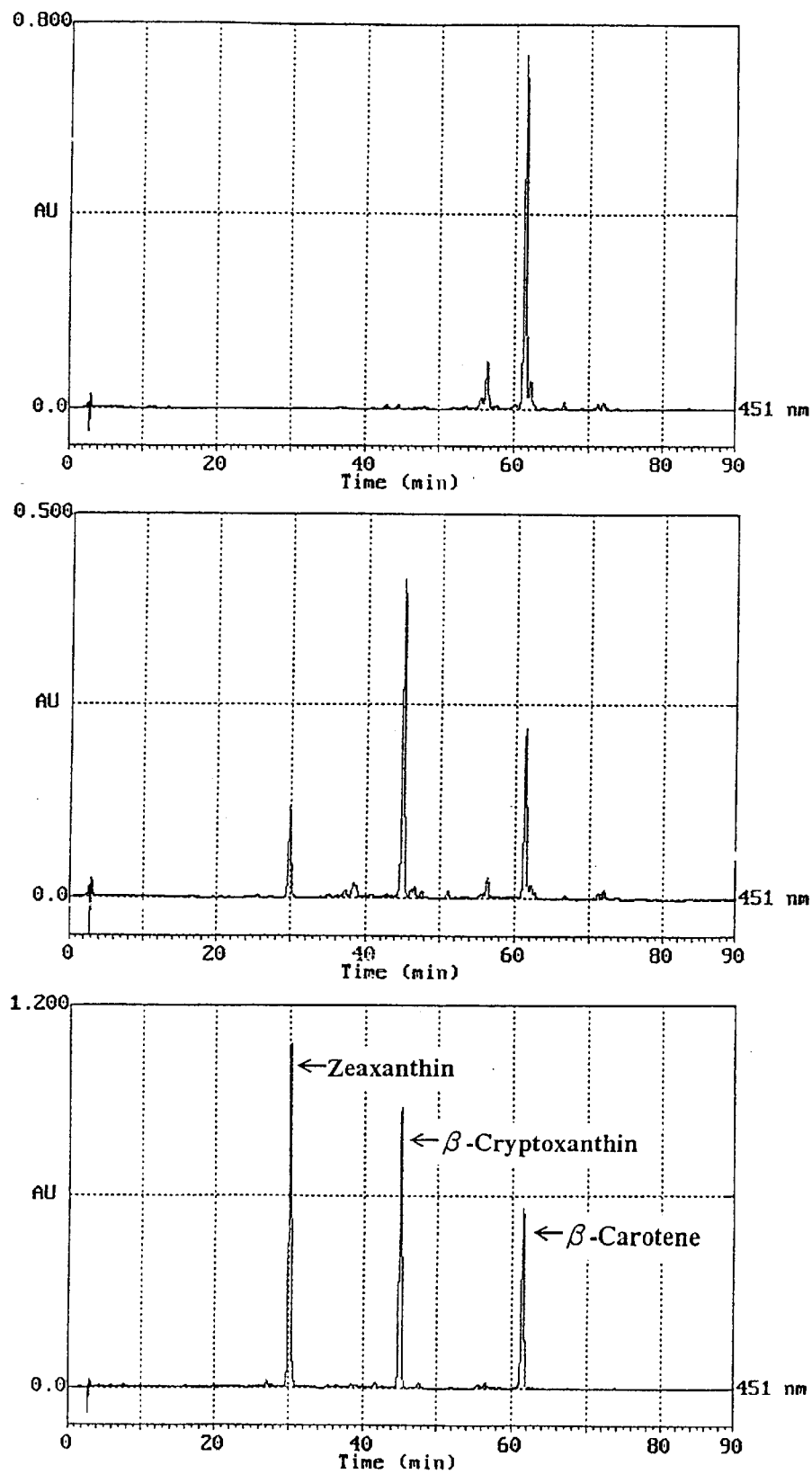
FIG. 2 presents chromatograms showing the results of high performance liquid chromatography.

As a result, the chromatograms shown in FIG. 2 were obtained. When the resultant peaks were compared with the peaks of the carotenoid standard products manufactured by Funakoshi, it was found that the *E. coli* produced β-cryptoxanthin, β-carotene and zeaxanthin at a ratio of 43:22:11. From this result, it was judged that the citrus-derived β-carotene hydroxylase mainly produces β-cryptoxanthin.

(2) Production and Identification of β-Cryptoxanthin

Plasmid pCitBECH 1-introduced, β-carotene-producing *E. coli* JM101 [*E. coli* (PACCAR16ΔcrtX, pCitBECH 1)] (presenting a yellow color) was cultured in 1.6 L of 2×YT medium [1.6% tryptone, 1% yeast extract, 0.5% NaCl] containing 150 µg/ml of ampicillin (Ap) and 30 µg/ml of chloramphenicol (Cm) at 30° C. for 28 hrs. Cells were harvested from the culture fluid were subjected to extraction with 360 ml of acetone. The resultant extract was concentrated and extracted with 200 ml of chloroform/methanol (9/1) twice, followed by concentration and drying. The resultant solid material was dissolved in a small amount of chloroform/methanol (9/1) and then subjected to thin layer chromatography (TLC) in which the sample was developed with chloroform/methanol on a silica gel preparative TLC plate from Merck.

As a result of this TLC, the initial pigments were divided into two spots of Rf values 0.4 (dark) and 0.1 (very light), respectively, in addition to the β-carotene spot at the top. Then, the dark yellow pigment of Rf 0.4 was scratched off from the TLC plate, dissolved in a small amount of chloroform/methanol (1/1) and subjected to TOYOPEARL HW-40 column chromatography for development and elution.

As a result, 1 mg of the pure pigment was obtained.

This pigment was considered to be β-cryptoxanthin from the results of examination of the ultraviolet-visible spectrum (λ 425, 448, 475 nm in methanol) and the FD-MS spectrum (m/e 553, [M]+). Further, two signals of 3-hydroxy-β-ionone ring and β-ionone ring (G. Englert, N.M.R. of Carotenoids edited by G. Britton, T. W. Goodwin, Carotenoid Chemistry and Biochemistry) were confirmed from its $^1$H-NMR spectrum.

Consequently, this pigment was identified as β-cryptoxanthin (FIG. 2). FIG. 2 indicates that the gene of the invention is involved in biosynthesis of β-cryptoxanthin. In FIG. 2, the top panel shows the results of HPLC analysis of the carotenoids produced by E. coli in which an Erwinia-derived β-carotene biosynthesis gene was incorporated; the middle panel shows the results of HPLC analysis of the carotenoids produced by the above E. coli in which the gene of the invention was further incorporated; and the bottom panel shows the results of HPLC analysis of zeaxanthin, β-cryptoxanthin and β-carotene standard products.

From FIG. 2, it can be seen that, different from conventional β-carotene hydroxylases encoded by known genes (Crt Z) derived from Erwinia and marine bacteria, the β-carotene hydroxylase encoded by the gene of the invention catalyzes synthesis of carotenoids in such a manner that β-cryptoxanthin is produced mainly and zeaxanthin is produced in only a small amount (FIG. 2, middle panel).

EFFECT OF THE INVENTION

According to the present invention, a β-catotene hydroxylase, a DNA coding for the β-catotene hydroxylase, a recombinant vector comprising the DNA, a transformant transformed with the vector, a method for preparing the ) β-catotene hydroxylase and a method for preparing β-cryptoxanthin are provided.

The β-catotene hydroxylase of the invention is useful in catalyzing synthesis of β-cryptoxanthin, a pigment necessary and important for maintaining the quality and function of citrus fruits and processed products thereof.

What is claimed is:

1. A DNA coding for a protien comprising the amino acid sequence as shown in SEQ ID NO:2.

2. The DNA according to claim 1, wherein said DNA comprises the nucleotide sequence as shown in SEQ ID NO:1.

3. A recombinant vector comprising the DNA according to claim 1 or 2.

4. A transformant which is transformed with the vector according to claim 3.

5. A method for preparing a β-carotene hydroxylase comprising culturing the transformant according to claim 4 in a medium and recovering the β-carotene hydroxylase from the resultant culture.

6. A method for preparing β-cryptoxanthin comprising culturing the transformant according to claim 4 in a medium and recovering β-cryptoxanthin from the resultant culture.

* * * * *

SEQUENCE LISTING

<160> NUMBER OF SEQ ID NOS: 8

<210> SEQ ID NO 1
<211> LENGTH: 1158
<212> TYPE: DNA
<213> ORGANISM: Citrus unshiu
<220> FEATURE:
<221> NAME/KEY: CDS
<222> LOCATION: (87)..(1019)

<400> SEQUENCE: 1

```
ccacaatcca cttcacatca actcttcctc ttttcaagtg cttttactct aaaacccaaa        60
acctcgtaaa caaacaaaac cccacc atg gcg gtc gga cta ttg gcc gcc ata       113
                              Met Ala Val Gly Leu Leu Ala Ala Ile
                                1               5 gtc ccg aag ccc ttc tgt ctc ctc aca aca aaa ctt caa ccc tct tcg        161
Val Pro Lys Pro Phe Cys Leu Leu Thr Thr Lys Leu Gln Pro Ser Ser
 10              15                  20                  25 ctc ctc aca aca aaa ccc gct ccc ctt ttt gcc cct ctc ggt acc cac        209
Leu Leu Thr Thr Lys Pro Ala Pro Leu Phe Ala Pro Leu Gly Thr His
                 30                  35                  40 cat ggc ttc ttt aat ggc aaa aac cga aga aaa ctc aac tct ttc acc        257
His Gly Phe Phe Asn Gly Lys Asn Arg Arg Lys Leu Asn Ser Phe Thr
             45                  50                  55 gta tgt ttt gtt tta gag gag aaa aaa caa agc acc cag atc gag act        305
Val Cys Phe Val Leu Glu Glu Lys Lys Gln Ser Thr Gln Ile Glu Thr
         60                  65                  70 ttc acg gac gag gag gag gag gag tcg ggt acc cag atc tcg act g   ct     353
Phe Thr Asp Glu Glu Glu Glu Glu Ser Gly Thr Gln Ile Ser Thr Ala
     75                  80                  85 gcc cgc gtg gcc gag aaa ttg gcg aga aag aga tcc gag agg ttc act        401
Ala Arg Val Ala Glu Lys Leu Ala Arg Lys Arg Ser Glu Arg Phe Thr
 90                  95                 100                 105 tat ctc gtt gct gcc gtc atg tct agt ttt ggt atc act tcc atg gct        449
Tyr Leu Val Ala Ala Val Met Ser Ser Phe Gly Ile Thr Ser Met Ala
                110                 115                 120
```

```
gtc atg gct gtt tat tac agg ttc tgg tgg caa atg gag ggt gga g   ag    497
Val Met Ala Val Tyr Tyr Arg Phe Trp Trp Gln Met Glu Gly Gly Glu
        125                 130                 135 gtg cct tta gct gaa atg ttt ggc aca ttt gct ctc tct gtt ggt gct       545
Val Pro Leu Ala Glu Met Phe Gly Thr Phe Ala Leu Ser Val Gly Ala
            140                 145                 150 gct gtg ggc atg gag ttt tgg gca cga tgg gct cat aaa gct ctg tgg       593
Ala Val Gly Met Glu Phe Trp Ala Arg Trp Ala His Lys Ala Leu Trp
        155                 160                 165 cat gct tct tta tgg cat atg cac gag tct cac cat cga cca aga g   ag    641
His Ala Ser Leu Trp His Met His Glu Ser His His Arg Pro Arg Glu
170                 175                 180                 185 ggt cct ttt gag cta aac gat gtg ttt gcc ata atc aac gca gtt cca       689
Gly Pro Phe Glu Leu Asn Asp Val Phe Ala Ile Ile Asn Ala Val Pro
                190                 195                 200 gcc ata gcc ctt ctc tct ttt ggc ttc ttc cac aaa ggc ctt gta cct       737
Ala Ile Ala Leu Leu Ser Phe Gly Phe Phe His Lys Gly Leu Val Pro
            205                 210                 215 ggt ctc tgc ttt ggt gct gga ctt ggc att acg gtg ttt ggg atg g   cc    785
Gly Leu Cys Phe Gly Ala Gly Leu Gly Ile Thr Val Phe Gly Met Ala
        220                 225                 230 tac atg ttc gtc cac gat ggt ctc gtt cac aaa agg ttc cct gtg ggt       833
Tyr Met Phe Val His Asp Gly Leu Val His Lys Arg Phe Pro Val Gly
    235                 240                 245 ccc att gcc gac gtg cct tat ttc cgg aga gtc gct gcg gct cac cag      881
Pro Ile Ala Asp Val Pro Tyr Phe Arg Arg Val Ala Ala Ala His Gln
250                 255                 260                 265 ctt cac cac tcg gat aaa ttc cac ggt gtt cca tat ggg ctc ttt c   tc    929
Leu His His Ser Asp Lys Phe His Gly Val Pro Tyr Gly Leu Phe Leu
                270                 275                 280 gga cct aag gag ctt gaa gaa gtg ggg gga cta gaa gaa ttg gag aag       977
Gly Pro Lys Glu Leu Glu Glu Val Gly Gly Leu Glu Glu Leu Glu Lys
            285                 290                 295 gag atc agt aag aga atc aaa tca tac aac agg gtt cca aaa              1019
Glu Ile Ser Lys Arg Ile Lys Ser Tyr Asn Arg Val Pro Lys
        300                 305                 310 taatcaattt aatgggagga ccaattttg gatcaatttg tcagtgtaca gaaacaatag     1079
tgttattaat gaaaaaaata aattatgaat gcttatgggt ggattactgt tgtaaagttt    1139
atgatgttaa ataatatat                                                1158

<210> SEQ ID NO 2
<211> LENGTH: 311
<212> TYPE: PRT
<213> ORGANISM: Citrus unshiu

<400> SEQUENCE: 2

Met Ala Val Gly Leu Leu Ala Ala Ile Val Pro Lys Pro Phe Cys Leu
 1               5                  10                  15

Leu Thr Thr Lys Leu Gln Pro Ser Ser Leu Thr Thr Lys Pro Ala
             20                  25                  30

Pro Leu Phe Ala Pro Leu Gly Thr His His Gly Phe Asn Gly Lys
         35                  40                  45

Asn Arg Arg Lys Leu Asn Ser Phe Thr Val Cys Phe Leu Glu Glu
     50                  55                  60

Lys Lys Gln Ser Thr Gln Ile Glu Thr Phe Thr Asp Glu Glu Glu
 65                  70                  75                  80

Glu Ser Gly Thr Gln Ile Ser Thr Ala Ala Arg Val Ala Glu Lys Leu
             85                  90                  95
```

```
Ala Arg Lys Arg Ser Glu Arg Phe Thr Tyr Leu Val Ala Ala Val Met
            100                 105                 110
Ser Ser Phe Gly Ile Thr Ser Met Ala Val Met Ala Val Tyr Tyr Arg
            115                 120                 125
Phe Trp Trp Gln Met Glu Gly Gly Glu Val Pro Leu Ala Glu Met Phe
        130                 135                 140
Gly Thr Phe Ala Leu Ser Val Gly Ala Val Gly Met Glu Phe Trp
145                 150                 155                 160
Ala Arg Trp Ala His Lys Ala Leu Trp His Ala Ser Leu Trp His Met
                165                 170                 175
His Glu Ser His His Arg Pro Arg Glu Gly Pro Phe Glu Leu Asn Asp
            180                 185                 190
Val Phe Ala Ile Ile Asn Ala Val Pro Ala Ile Ala Leu Leu Ser Phe
            195                 200                 205
Gly Phe Phe His Lys Gly Leu Val Pro Gly Leu Cys Phe Gly Ala Gly
            210                 215                 220
Leu Gly Ile Thr Val Phe Gly Met Ala Tyr Met Phe Val His Asp Gly
225                 230                 235                 240
Leu Val His Lys Arg Phe Pro Val Gly Pro Ile Ala Asp Val Pro Tyr
                245                 250                 255
Phe Arg Arg Val Ala Ala Ala His Gln Leu His His Ser Asp Lys Phe
            260                 265                 270
His Gly Val Pro Tyr Gly Leu Phe Leu Gly Pro Lys Glu Leu Glu Glu
            275                 280                 285
Val Gly Gly Leu Glu Glu Leu Glu Lys Glu Ile Ser Lys Arg Ile Lys
    290                 295                 300
Ser Tyr Asn Arg Val Pro Lys
305                 310
```

```
<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Peptide
      designed based on the highly conserved amino acid
      sequence of beta-carotene hydroxylase

<400> SEQUENCE: 3

Phe Glu Leu Asn Asp Val Phe Ala
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Peptide
      designed based on the highly conserved amino acid
      sequence of beta-carotene hydroxylase

<400> SEQUENCE: 4

His Asp Gly Leu Val His
 1               5

<210> SEQ ID NO 5
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      DNA
<220> FEATURE:
<221> NAME/KEY: misc_feature
<222> LOCATION: (1)..(18)
<223> OTHER INFORMATION: y = c or t; r = a or g; n = g, a, c, or t

<400> SEQUENCE: 5
ttygarctaa aygaygtn                                                    18

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: misc_feature
<222> LOCATION: (1)..(17)
<223> OTHER INFORMATION: y = c or t; n = g, a, c, or t

<400> SEQUENCE: 6
cacgayggtc tngtnca                                                     17

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
aactggaaga attcgcggcc gcaggaattt tttttttttt ttttt                      45

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
tggaagaatt cgcggccgca g                                                21
```